United States Patent [19]
Weg

[11] Patent Number: 5,543,434
[45] Date of Patent: Aug. 6, 1996

[54] NASAL ADMINISTRATION OF KETAMINE TO MANAGE PAIN

[76] Inventor: Stuart L. Weg, 498 Island Way, Franklin Lakes, N.J. 070417

[21] Appl. No.: 201,756

[22] Filed: Feb. 25, 1994

[51] Int. Cl.$^6$ ............................................. A61K 31/135
[52] U.S. Cl. ........................................................ 514/647
[58] Field of Search ................................. 514/646, 647

[56] References Cited

U.S. PATENT DOCUMENTS

| | | | |
|---|---|---|---|
| 4,334,526 | 6/1982 | Hamacher | 128/1 R |
| 4,671,953 | 6/1987 | Stanley et al. | 424/440 |
| 5,112,804 | 5/1993 | Kowarski | 514/3 |
| 5,132,114 | 7/1992 | Stanley et al. | 424/440 |

FOREIGN PATENT DOCUMENTS

WO93/15737  8/1993  WIPO .

OTHER PUBLICATIONS

Aldrete et al. (1988)Acta Anaesthesiol. Belg. 39 (No.3, Sup.2):95–6.
(1990) West. J. Med. 153:311–2.
(1980) J. Pediatr. Ophthalmol. Strabismus. 17:292–6.
Trujillo and Akil. 1994. Brain Res. 633:178–88.
Abram. 1993. Reg. Anesth. 18 (suppl):406–13.
Louon et al. 1993. Br. J. Opthalmol. 77:529–30.
Jansen. 1993. Brit. Med. J. 306:601–02.
Stannard and Porter. 1993. Pain 54:227–30.
Weksler et al. 1993. Can. J. Anaesthia 40:119–21.
Adams and Hempelmann. 1990. Anasthesist 39:71–76. (English abstract only).
Oshima et al. 1990. Can. J. Anaesth. 37:385–92.
Reich and Silvay. 1989. Can. J. Anaesth. 36:186–97.
Sadove et al. 1971. Anesth. Analg. 50:452–57.
Bovill and Dundee. 1971. Br. J. Anaesth. 43:496–94.
Domino et al. 1965. Clin. Pharmacol. Ther. 6:279–91.
Remington's Pharmaceutical Sciences, 16th ed. (1980) pp.1445, 1552.

*Primary Examiner*—Raymond J. Henley, III
*Assistant Examiner*—Phyllis G. Spivack
*Attorney, Agent, or Firm*—Klauber & Jackson

[57] ABSTRACT

The invention relates to self-management of pain on an outpatient basis comprising administering via a nasal route a dose of ketamine effective to alleviate pain to a subject suffering from pain.

21 Claims, No Drawings

NASAL ADMINISTRATION OF KETAMINE TO MANAGE PAIN

FIELD OF THE INVENTION

The present invention relates to the management of chronic pain without requiring administration of narcotics. The invention also relates to self-management of pain on an outpatient basis.

BACKGROUND OF THE INVENTION

Ketamine ((2-(2-chlorophenyl)-2-(methylamino)-cyclohexanone) is a general anesthetic used by anesthesiologists, veterinarians, and researchers. Nasal administration of ketamine and midazolam to achieve sedation for ophthalmic surgery, and to induce anesthesia prior to elective surgery in healthy children has been reported (Louon et al., 1993, Br. J. Ophthalmol. 77:529–530; Weksler et al., 1993, Can. J. Anaesthesia 40:119–121). Usually, ketamine is administered intramuscularly (i.m.) or intravenously (i.v.) to induce anesthesia.

Ketamine has also been known to have analgesic properties (Domino et al., 1965, Clin. Pharmacol. Ther. 6:279); analgesia can be achieved with subanesthetic doses of ketamine (Bovill, 1971, Br. J. Anaesth. 43:496; Sadove et al., 1971, Anesth. Analg. 50:452–457). The drug is administered by various routes, including i.v., i.m., caudal, intrathecal, and subcutaneous (s.c.). Subcutaneous administration of ketamine has been used to treat pain following surgery and associated with terminal cancer (see, e.g., Oshima et al., 1990, Can. J. Anaesth. 37:385–386). Ketamine hydrochloride administered via a subcutaneous cannula was reported to successfully treat phantom limb pain (Stannard and Porter, 1993, Pain 54:227–230).

Management of pain, and particularly chronic pain, is complex and frequently unsuccessful. The first line of treatment usually involves administration of μ-opioid agonists, e.g., narcotics such as morphine (see, e.g., Anderson and Brill, 1992, Semin. Anesth. 11:158–171). However, rapid tolerance and marked resistance to narcotics frequently develop, thus rendering these agents ineffective (see, e.g., Abram, 1993, Reg. Anesth. 18(SUPPL):406–413). Noncompetitive N-methyl-D-aspartate (NMDA) receptor antagonists, including ketamine, have been reported to interfere with the development of tolerance to the analgesic effects of morphine, possibly through blockade of the NMDA receptor rather than from "side-effects" of the antagonist, since the antagonists were not found to reverse tolerance (Trujillo and Akil, 1994, Brain Res. 633:178–188).

Often, pain management involves administration of a plethora of drugs, such as narcotics, agonist-antagonist agents, butorphanols, benzodiazepines, GABA stimulators, barbiturates, barbiturate-like drugs, orally, e.g., in a pill or liquid formulation, or by i.v. or i.m. injection. Opioid agonists and antagonists may be combined. Thus, a combination of drugs can have offsetting effects. More problematic is the possibility of adverse side effects, particularly gastric distress that accompanies oral administration, or the fear that injections can inspire.

Frequently, a patient suffering from chronic pain will require medication to control stomach and other gastric problems as a result of oral administration of drugs. Alternatives to oral self-administration for most of the analgesic and sedative medications for the treatment of chronic pain in addition to perioral administration are not common, can be cumbersome (e.g., i.v. or s.c. administration requires use of a cannula or needle), and generally require medical training.

U.S. Pat. No. 4,671,953 describes the administration of sedative, analgesic or sedative drugs in a candy matrix, such that the drug enters the bloodstream through the oral mucosal membranes. However, this method suffers from the disadvantage that a sedated patient may fall asleep with the candy remaining in his or her mouth, which can result in choking. Furthermore, because the total dose of the drug in the candy may exceed the desired dose, administration of the candy must be medically supervised. Finally, the candy is simply unsuitable for everyday use, as sucking on a lollipop is an unseemly practice for an employee or business person.

Moreover, when administration is under the control of the patient suffering from pain, i.e., on an outpatient basis, the potential for overdosing or abuse exists, particularly with respect to narcotics.

Thus, there is a need in the art for management of pain using non-opioid drugs.

There is a further need in the art for a rapid method for reducing or eliminating breakthrough pain that is refractory to standard treatment regimens.

There is a further need in the art to avoid oral and injection administration of pain medication.

There is a need in the art for a fast, convenient, and socially acceptable method for patient self-administration of medication to manage or control pain.

There is yet a further need in the art to avoid overdose and abuse of self-administered medication.

These and other needs in the art have been addressed by the instant invention, which is based on the inventor's discovery that ketamine can surprisingly be administered nasally to alleviate pain safely and effectively, in conjunction with or independently of other pain management regimens.

The citation or identification of any reference in this application shall not be construed as an admission that such reference is available as prior art to the present invention.

SUMMARY OF THE INVENTION

The present invention is broadly directed to a method for treating pain in a subject comprising administering via a nasal route a dose of ketamine effective to alleviate pain to a subject suffering from pain. In a further embodiment, the present invention provides for pulmonary administration of ketamine by inhalation. Nasal administration of an analgesic dose of ketamine advantageously allows for patient self administration of the drug, which provides for pain management on an outpatient basis. Moreover, ketamine administration in nasal sprays and inhalers are generally socially acceptable.

Pain therapy on an outpatient basis advantageously reduces the demands on hospital services, results in a substantial decrease in the cost of treatment, and provides the patient with a more normal living and working environment, which can positively affect treatment outcome.

Another advantage of the invention is that it avoids the need to administer narcotic agents for the treatment of chronic pain. Although effective analgesics, narcotics can lose effectiveness due to tolerance or resistance. Narcotics are also highly addictive.

A further advantage of the invention is that it avoids administration in a candy, which requires medical supervision and is socially questionable, if not outright unacceptable.

Yet a further advantage of the invention is that ketamine is an inexpensive, readily available drug, with minor adverse side effects. Thus, the invention contemplates additional savings to the overburdened health care system.

Nasal administration of ketamine is rapid, allowing for fast action of the drug, and easily accomplished by a non-medically trained patient.

In one aspect, the pain-alleviating dose of ketamine is approximately 0.01 to approximately 1 mg/kg of body weight. In a more preferred aspect, the dose of ketamine is approximately 0.05 to approximately 0.7 mg/kg of body weight. In another embodiment, the total dose of ketamine per nasal administration ranges from about 1 to about 30 mg.

In a specific aspect of the invention, the dose of ketamine is effective to alleviate breakthrough pain in a patient suffering from a chronic pain condition.

In another specific aspect of the invention, the dose of ketamine is effective to alleviate breakthrough pain associated with labor, particularly transition labor.

In a particular aspect, nasal administration of ketamine can be a supplemental therapy in a pain management regimen that include administration of one or more of narcotics, analgesics, and sedatives, e.g., as described above.

The present invention further contemplates administering a dose of a benzodiazepine effective to inhibit dysphoria that can be associated with administration of high doses of ketamine. In a preferred aspect, the benzodiazepine is administered nasally with the ketamine.

It should be noted that a further advantage of the instant invention is that it avoids dosing a patient with dysphoric or hallucinogenic amounts of ketamine by providing a metered, analgesic dose, which is well below the level associated with dysphoria or hallucination.

In yet a further embodiment, the present invention contemplates administering a dose of a narcotic analgesic effective to alleviate pain with the ketamine; preferably the narcotic analgesic is administered via the mucosal route with the ketamine.

Accordingly, the invention provides a device for patient self-administration of ketamine. In its broadest aspect, the device of the invention comprises a nasal inhaler containing an aerosol formulation of ketamine and a pharmaceutically acceptable dispersant, wherein the device is metered to disperse an amount of the aerosol formulation that contains a dose of ketamine effective to alleviate pain. The dispersant may be a surfactant, such as, but not limited to, polyoxyethylene fatty acid esters, polyoxyethylene fatty acid alcohols, and polyoxyethylene sorbitan fatty acid esters.

In one specific embodiment, the aerosol formulation is a dry powder aerosol formulation in which the ketamine is present as a finely divided powder. The dry powder formulation can further comprise a bulking agent, such as, but not limited to, lactose, sorbitol, sucrose and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises a benzodiazepine in a concentration such that the metered amount of the aerosol formulation dispersed by the device contains a dose of the benzodiazepine effective to inhibit dysphoria, or a narcotic in a concentration such that the metered amount of the aerosol formulation dispersed by the device contains a dose of the narcotic effective to alleviate pain. The present invention further contemplates including both a benzodiazepine and a narcotic in the aerosol formulation.

Thus, it is an object of the invention to provide for self administration of a safe, non-narcotic drug for outpatient treatment of pain.

It is a further object of the present invention to provide a method for nasal administration of a drug in a controlled amount for the treatment of pain.

Yet a further object of the invention is to provide a device that can be used outside a hospital or medical office by non-medical personnel for nasal self administration of ketamine.

These and other objects of the present invention will become more readily apparent by reference to the following detailed description.

DETAILED DESCRIPTION OF THE INVENTION

In its primary aspect, the present invention relates to nasal administration of ketamine for the treatment of pain. In a more preferred aspect, the invention provides a method and device for patient self administration of ketamine for pain management.

The invention can alleviate pain from many causes, including but not limited to shock; limb amputation; severe chemical or thermal burn injury; sprains, ligament tears, fractures, wounds and other tissue injuries; dental surgery, procedures and maladies; labor and delivery; during physical therapy; post operative pain; radiation poisoning; cancer; acquired immunodeficiency syndrome (AIDS); epidural (or peridural) fibrosis; failed back surgery and failed laminectomy; sciatica; painful sickle cell crisis; arthritis; autoimmune disease; intractable bladder pain; and the like. Mucosal administration of ketamine is also amenable to hospice use, particularly hospices that specialize in the care of cancer and AIDS patients.

In one embodiment, nasal administration of ketamine can relieve or alleviate episodes of acute breakthrough pain that can occur in a chronic pain condition. In a further embodiment, nasal administration of ketamine can be used as an adjunct therapy to a conventional treatment regimen for a chronic pain condition to alleviate breakthrough pain.

A particular advantage of the present invention for reducing labor and delivery pain is that ketamine in low doses is not known to have significant adverse effects on the fetus.

In a related embodiment, nasal administration can be used as an adjunct or directly to treat an acute asthma attack. Since unrelated pain conditions can induce asthma, the present invention advantageously provides for alleviating pain, thus blocking the cause of the attack. Furthermore, ketamine (in contrast to narcotic pain medications) is a bronchodilator.

In yet another related embodiment, nasal administration of ketamine can be used in the treatment of acute nausea. Nasal ketamine is particularly attractive for this condition, as nausea precludes the use of oral medications. In particular, nasal ketamine can alleviate pain that may be causing the nausea, and can alleviate the abdominal pain that frequently accompanies sever nausea.

In yet a further related embodiment, nasal administration of ketamine can be used to treat acute agitation, for example, agitation exhibited by an alcohol or drug intoxicated individual, or by a person placed under arrest by the police.

Similarly, nasal ketamine may be useful in the treatment of shock resulting from severe injuries. Thus, even if a patient fails to sense pain because of severe shock, the extreme pain associated with a severe injury contributes to shock.

The present invention is based on the surprising and unexpected discovery that nasal administration of ketamine can alleviate symptoms of chronic pain. Thus, in a specific Example, infra, a patient suffering from intractable bladder pain, and taking a variety of narcotics, analgesics, and sedatives in an unsuccessful attempt to control the pain, was able to achieve more satisfactory pain management by nasal administration of 16–32 mg of ketamine, corresponding to [0.26 to 0.53] mg/kg of body weight. The dosage was effective for about 15 minutes to about 1 hour in alleviating pain. The patient was able to reduce the amount of a oral pain medications, which had caused gastric distress.

Accordingly, the present invention is directed of methods for alleviating chronic pain on an outpatient basis by nasal administration of ketamine, and to devices usable by non-medical personnel for nasal self-administration of ketamine.

Ketamine will preferably be prepared in a formulation or pharmaceutical composition appropriate for nasal administration. Suitable formulations are discussed in detail, infra. In a further embodiment, ketamine can be formulated with a mucosal penetration enhancer to facilitate delivery of the drug. The formulation can also be prepared with pH optimized for solubility, drug stability, absorption through nasal mucosa, and other considerations.

The invention provides for administration of a therapeutically effective dose of ketamine, i.e., a dose effective to alleviate pain. The actual dose will vary, depending on the body weight of the patient, the severity of the pain, the route of administration, the nature of medications administered concurrently, the number of doses to be administered per day, and other factors generally considered by the ordinary skilled physician in the administration of drugs. In a specific embodiment, the amount of ketamine administered to a patient suffering from chronic pain is about 10% to about 20% of the amount used to induce anesthesia. In another specific embodiment, the dose of ketamine is about 0.01 mg per kg of body weight (0.01 mg/kg) to about 1 mg/kg; preferably about 0.05 mg/kg to about 0.7 mg/kg. In yet another embodiment, the dose ranges from about 1 mg to about 30 mg. Preferably, the effective dose is titrated under the supervision of a physician or medical care provider, so that the optimum dose for the particular application is accurately determined. Thus, the present invention provides a dose suited to each individual patient.

Once the dosage range is established, a further advantage of the invention is that the patient can administer ketamine on an as-needed, dose-to-effect basis. Thus, the frequency of administration is under control of the patient. However, the relatively low dose with each administration will reduce the possibilities for abuse.

Yet another particular advantage of the present invention is that nasal administration of ketamine is non-invasive, and provides for introduction into the bloodstream almost as fast as i.v. administration, and much faster than perioral administration.

More importantly, a patient can control administration of the pain medication, because nasal administration provides for precise control over the dosage and effect of the drug used to offset changes in activity and pain levels throughout a day. Nasal administration of ketamine optimally provides for dose-to-effect administration of the drug.

Thus, according to the invention, the patient can safely administer an amount of drug effective to alleviate pain by controlling the amount and frequency of administration of a formulation according to the invention. Safe patient regulated control of pain medication is an important advantage because pain is such a subjective condition. The advantage is two-fold here, as the patient can effectively alleviate pain, and the power to alleviate the pain will have significant psychological benefits. A positive psychological attitude can significantly improve the course and outcome of a treatment regimen, as well as making the entire process more bearable to the patient.

Various terms are used throughout the specification, which are defined herein:

The term "mucosal" refers to a tissue comprising a mucous membranes, such as the nasal mucosa and the pulmonary mucosa.

The term "nasal administration" in all its grammatical forms refers to administration of a drug through the nasal mucous membrane to the bloodstream for systemic delivery of the drug. The advantages of nasal administration for drug delivery are that it does not require injection using a syringe and needle, it avoids necrosis that can accompany i.m. administration of drugs, it avoids the need to constantly such on a lollipop, and trans-mucosal administration of a drug is highly amenable to self administration.

The present invention further contemplates pulmonary administration through an inhaler in a particular aspect.

The term "mucosal penetration enhancer" refers to a reagent that increases the rate or facility of transmucosal penetration of ketamine, such as but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol.

A "therapeutically effective amount" of a drug is an amount effective to demonstrate a desired activity of the drug. According to the instant invention, a therapeutically effective amount of ketamine is an amount effective to alleviate, i.e., noticeably reduce, pain in a patient.

The invention will now be described in greater detail, with reference to nasal and pulmonary administration of ketamine and additional therapeutically active drugs or agents with which ketamine can be administered.

The present invention contemplates formulations comprising ketamine for use in a wide variety of devices that are designed for the delivery of pharmaceutical compositions and therapeutic formulations to the respiratory tract, preferably the nasal passages. The preferred route of administration of the present invention is in an aerosol spray for nasal inhalation. Ketamine, combined with a dispersing agent, or dispersant, can be administered in an aerosol formulation as a dry powder or in a solution or suspension with a diluent.

As used herein, the term "aerosol" refers to suspension in the air. In particular, aerosol refers to the particlization or atomization of a formulation of the invention and its suspension in the air. According to the present invention, an aerosol formulation is a formulation comprising ketamine for nasal inhalation or pulmonary administration.

As used herein, the term "inhaler" refers both to devices for nasal and pulmonary administration of a drug, e.g., in solution, powder and the like. For example, a the term "inhaler" is intended to encompass a propellant driven inhaler, such as is used for to administer antihistamine for acute asthma attacks, and plastic spray bottles, such as are used to administer decongestants.

As used herein, the term "dispersant" refers to a agent that assists aerosolization of the ketamine or absorption of the ketamine in mucosal tissue, or both. In a specific aspect, the dispersant can be a mucosal penetration enhancer. Preferably, the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans.

Suitable dispersing agents are well known in the art, and include but are not limited to surfactants and the like. For example, surfactants that are generally used in the art to reduce surface induced aggregation of ketamine caused by atomization of the solution forming the liquid aerosol may be used. Nonlimiting examples of such surfactants are surfactants such as polyoxyethylene fatty acid esters and alcohols, and polyoxyethylene sorbitan fatty acid esters. Amounts of surfactants used will vary, being generally within the range or 0.001 and 4% by weight of the formulation. Suitable surfactants are well known in the art, and can be selected on the basis of desired properties, depending on the specific formulation, concentration of ketamine, diluent (in a liquid formulation) or form of powder (in a dry powder formulation), etc.

The liquid aerosol formulations contain ketamine and a dispersing agent in a physiologically acceptable diluent. The dry powder aerosol formulations of the present invention consist of a finely divided solid form of ketamine and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

In a particular embodiment, the mass median dynamic diameter will be 5 micrometers or less in order to ensure that the drug particles reach the lung alveoli (Wearley, L. L., 1991, 1991, Crit. Rev. in Ther. Drug Carrier Systems 8:333).

With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

As noted above, in a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

For nasal administration, a useful device is a small, hard bottle to which a metered dose sprayer is attached. In one embodiment, the metered dose is delivered by drawing the ketamine solution into a chamber of defined volume, which chamber has an aperture dimensioned to aerosolize and aerosol formulation by forming a spray when a liquid in the chamber is compressed. The chamber is compressed to administer the ketamine. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Often, the aerosolization of a liquid or a dry powder formulation for inhalation into the lung will require a propellent. The propellent may be any propellant generally used in the art. Specific nonlimiting examples of such useful propellants are a chloroflourocarbon, a hydrofluorocarbon, a hydochlorofluorocarbon, or a hydrocarbon, including trifluoromethane, dichlorodiflouromethane, dichlorotetrafluoroethanol, and 1,1,1,2-tetraflouroethane, or combinations thereof.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–22 and can be used in connection with the present invention.

In a further embodiment, as discussed in detail infra, an aerosol formulation of the present invention can include other therapeutically or pharmacologically active ingredients in addition to ketamine, such as but not limited to a benzodiazepine or a narcotic analgesic.

In general, as described in detail infra, ketamine is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of ketamine in an aerosol formulation of the invention.

Liquid Aerosol Formulations

The present invention provides aerosol formulations and dosage forms for use in treating subjects suffering from pain. In general such dosage forms contain ketamine in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactants and excipients.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising ketamine and another therapeutically effective drug, such as a benzodiazepine or a narcotic analgesic.

Aerosol Dry Powder Formulations

It is also contemplated that the present aerosol formulation can be prepared as a dry powder formulation comprising a finely divided powder form of ketamine and a dispersant.

In another embodiment, the dry powder formulation can comprise a finely divided dry powder containing ketamine, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising ketamine and another therapeutically effective drug, such as a benzodiazepine or a narcotic analgesic.

Additional Therapeutically Active Drugs or Agents

As note above, the invention contemplates coordinate nasal administration of ketamine with a therapeutically effective amount of another drug, in particular a benzodiazepine or a narcotic analgesic.

Co-administration of ketamine with a benzodiazepine is indicated to counteract the potential dysphoric or hallucinogenic effects of high dose administration of ketamine. Thus, a therapeutically effective amount of a benzodiazepine is an amount effective to inhibit dysphoria. In a further embodiment, an amount of a benzodiazepine also effective to sedate the patient may be administered.

The mild adverse effects of ketamine, e.g., dysphoria and/or hallucinations, sometimes called "ketamine dreams," can occur upon administration of a dose of greater than 50 mg of ketamine, and usually require doses greater than 100 mg per kg of ketamine. One advantage of the present invention is that nasal delivery of ketamine allows for control of the dose to a level effective for analgesia, but below the level that results in dysphoria. However, it is possible that an individual may overdose, particularly in response to an acute episode of pain. Thus, co-administration of a benzodiazepine may be indicated in certain circumstances.

Benzodiazepines that may be administered according to the present invention include, but are not limited to, flurazepam (Dalmane), diazepam (Valium), and preferably, Versed. In a preferred aspect, the transmucosal formulation of the invention comprises ketamine and a benzodiazepine, each present in a therapeutically effective amount.

In a preferred embodiment, a therapeutically effective amount of a narcotic analgesic used for the treatment of chronic pain is administered in conjunction with ketamine. A therapeutically effective amount of a narcotic drug is an amount effective to alleviate pain. Such narcotics include, but are not limited to, fentanyl, meperidine (Demoral), morphine and its narcotic analogs and derivatives such as hydromorphine (Dilaudid), and the like. In a preferred aspect, the transmucosal formulation of the invention comprises ketamine and a narcotic, each present in a therapeutically effective amount.

The invention can be better understood by referring to the following example, which is provided merely by way of exemplification and is not intended to limit the invention.

EXAMPLE

A female patient, age 40, weighing approximately 60 kg, presented with intractable bladder pain (interstitial cystitis), which had been diagnosed 4–5 months previously. Pain management in this patient consisted of 100 mg Demoral every 3 hours; Dilaudid 2–4 mg every 4 hours; Dalmane 30 mg per day; Duralgesic patches (fentanyl transdermal patches); bladder washes with Pyridium (phenazopyridine HCl), which is a urinary tract analgesic; and belladonna and opiate suppositories. In addition to the pain medication, the patient took Zantac and Tagamet to alleviate gastric distress, and Compazine (an anti-emetic) to counteract nausea. Gastric distress and nausea in this patient resulted from the pain medication.

Despite the dosages and range of pain medications used by this patient, satisfactory pain management was not achieved.

A diagnostic pre-sacral, or ilio-hypogastric, nerve block was performed on this patient to alleviate the pain. Unfortunately, the effect of the block was temporary, and the block was associated with significant motor weakness. After the block wore off, the patient stated that she was unable to function, as the most mundane activities were exhausting.

Ketamine (10 mg/cc) drops were administered i.v. over one hour, for a total dose of 40 mg ketamine. This resulted in reduction of the pain level by a factor of 2 (from #20 to about #10–12) as subjectively evaluated by the patient. About 1 hour after ketamine infusion was discontinued, the patient reported that the level of pain had increased to about #15, and thereafter rapidly to its previous level. The patient continued to take the other pain medications without effect.

Four days after the ketamine i.v. challenge, a 5 ml bottle containing 100 mg/ml ketamine solution was prepared. A single spray from the bottle delivered approximately $\frac{1}{6}$ ml of solution, i.e., 16 mg of ketamine. The patient was instructed to self-administer 1–2 sprays from the bottle for severe pain. The nasal spray bottle was prepared in order to provide sustainable pain medication on an outpatient basis.

The patient has demonstrated remarkable pain management with nasal administration of ketamine. Nasal ketamine has been particularly effective for control of breakthrough pain. The patient has decreased the amount of the other pain medications.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for self-treating pain in a subject comprising self-administering nasally on an outpatient basis a dose of ketamine of approximately 0.01 to approximately 1 mg/kg of body weight, which is effective to alleviate pain but below a dose that induces dysphoria by a subject suffering from pain.

2. The method according to claim 1, wherein the dose of ketamine is approximately 10% to approximately 20% of the dose used to induced anesthesia.

3. The method according to claim 1, wherein the dose of ketamine is approximately 0.05 to approximately 0.7 mg/kg of body weight.

4. The method according to claim 1, comprising administering the effective dose of ketamine to alleviate breakthrough pain.

5. The method according to claim 1, comprising administering the effective dose of ketamine to alleviate pain associated with labor and childbirth.

6. The method according to claim 1, comprising administering the effective dose of ketamine to alleviate chronic pain.

7. The method according to claim 1, comprising administering the effective dose of ketamine every 15 minutes to 1 hour.

8. The method according to claim 1, wherein the ketamine is administered in conjunction with a narcotic analgesic effective to alleviate pain.

9. The method according to claim 8, further comprising decreasing a dose of the narcotic analgesic.

10. A method for self-treating pain in a subject comprising self-administering nasally on an outpatient basis a dose of ketamine effective to alleviate pain by a subject suffering from pain, which dose of ketamine is determined by a physician or medical care provider to be below a level that induces dysphoria.

11. The method according to claim 10, wherein the dose of ketamine is approximately 10% to approximately 20% of the dose used to induce anesthesia.

12. A device for patient self-administration of ketamine on an outpatient basis comprising a nasal spray inhaler containing an aerosol spray formulation of ketamine and a pharmaceutically acceptable dispersant wherein the device is metered to disperse an amount of the aerosol formulation by forming a spray that contains a dose of ketamine of approximately 0.01 to approximately 1 mg/kg of body weight, which is effective to alleviate pain but below a dose that induces dysphoria.

13. The device of claim 12, wherein the dose of ketamine is approximately 10% to approximately 20% of the dose used to induce anesthesia.

14. The device of claim 12, wherein the dose of ketamine is approximately 0.05 to approximately 0.7 mg/kg of body weight.

15. The device of claim 12, wherein the dispersant is a surfactant.

16. The device of claim 12, wherein the aerosol formulation is a dry powder aerosol formulation in which the ketamine is present as a finely divided powder, and further comprising a bulking agent.

17. The device of claim 16, wherein the bulking agent is selected from the group consisting of lactose, sorbitol, sucrose and mannitol.

18. The device of claim 12, wherein the aerosol formulation is a liquid aerosol formulation further comprising a pharmaceutically acceptable diluent.

19. The device of claim 18, wherein the diluent is selected from the group consisting of sterile water, saline, buffered saline and dextrose solution.

20. A device for patient self-administration of ketamine comprising a nasal spray inhaler containing an aerosol spray formulation of ketamine and a pharmaceutically acceptable dispersant, wherein the device is metered to disperse an amount of the aerosol formulation by forming a spray that contains a dose of ketamine effective to alleviate pain but which dose of ketamine is determined by a physician or medical care provider to be below a level that induces dysphoria.

21. The device of claim 20, wherein the dose of ketamine is approximately 10% to approximately 20% of the dose used to induce anesthesia.

* * * * *